United States Patent [19]

Krespan

[11] Patent Number: 5,057,586

[45] Date of Patent: Oct. 15, 1991

[54] HALOGENATED 1,3-DIOXOLANES AND DERIVATIVES

[75] Inventor: Carl G. Krespan, Wilmington, Del.

[73] Assignee: E. I. Du Pont de Nemours and Company, Wilmington, Del.

[21] Appl. No.: 574,876

[22] Filed: Aug. 30, 1990

Related U.S. Application Data

[62] Division of Ser. No. 274,435, Nov. 22, 1988, Pat. No. 4,973,714, which is a division of Ser. No. 80,473, Jul. 31, 1987, Pat. No. 4,810,806.

[51] Int. Cl.$^5$ .............................................. C08F 16/12
[52] U.S. Cl. .................................... 526/247; 428/514
[58] Field of Search ...................... 526/247; 428/514

[56] References Cited

U.S. PATENT DOCUMENTS

| | | | |
|---|---|---|---|
| 2,925,424 | 2/1960 | Simmons | 260/340.7 |
| 3,308,107 | 3/1967 | Selman et al. | 260/87.5 |
| 3,316,216 | 4/1967 | Fawcett et al. | 260/63 |
| 3,324,144 | 6/1967 | Coe et al. | 260/340.9 |
| 3,379,736 | 4/1968 | Dietrich et al. | 260/340.9 |
| 3,450,716 | 6/1969 | Selman | 260/340.2 |
| 3,532,725 | 11/1970 | Dorfman et al. | 260/404 |
| 3,555,100 | 1/1971 | Garth et al. | 260/615 |
| 3,557,165 | 1/1971 | Dorfman et al. | 260/404 |
| 3,749,791 | 7/1973 | Terrell et al. | 424/278 |
| 3,865,845 | 2/1975 | Resnick | 260/340.9 |
| 3,978,030 | 8/1976 | Resnick | 526/247 |
| 4,182,718 | 1/1980 | Crutchfield et al. | 260/340.7 |
| 4,287,124 | 9/1981 | Siegemund et al. | 260/340.9 |
| 4,393,227 | 7/1983 | Squire | 549/455 |
| 4,399,264 | 8/1983 | Squire | 526/247 |
| 4,429,143 | 1/1984 | Anderson et al. | 549/450 |
| 4,431,786 | 2/1984 | Squire | 526/247 |
| 4,496,750 | 1/1985 | Anderson et al. | 549/455 |

OTHER PUBLICATIONS

*Journal of the American Chemical Society,* 82, 2288 (1960).

*Primary Examiner*—Joseph L. Schofer
*Assistant Examiner*—Alex H. Walker

[57] ABSTRACT

There are disclosed halogenated dioxolanes of a specified formula, dioxoles made therefrom, polymers of the dioxoles, and processes for making the dioxolanes.

8 Claims, No Drawings

HALOGENATED 1,3-DIOXOLANES AND DERIVATIVES

This is a divisional application of U.S. Ser. No. 07/274,435, filed Nov. 22, 1988, now U.S. Pat. No. 4,973,714, which is a divisional of U.S. Ser. No. 07/080,473, filed July 31, 1987, now U.S. Pat. No. 4,810,8.

BACKGROUND OF THE INVENTION

1. Field of the Invention

This invention relates to halogenated dioxolanes and dioxoles, their preparation and polymers of the dioxoles.

2. References

U.S. Pat. No. 2,925,424 issued to Simmons on Feb. 16, 1960, discloses cyclic fluoroketals of the formula

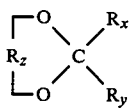

prepared by reacting fluoroketones with β-haloethanol; wherein $R_x$ and $R_y$ are perhalohydrocarbyl radicals of 1 to 7 carbon atoms, and $R_z$ is a divalent hydrocarbyl or halohydrocarbyl radical of 1 to 12 carbon atoms.

U.S. Pat. No. 3,308,107, issued to Selman, et al., on March 7, 1967, discloses perfluoro-2- methylene-4-methyl-1,3-dioxolane, its preparation from perfluoro-2,4-dimethyl-2-fluoroformyl-1,3-dioxolane, and polymers thereof.

U.S. Pat. No. 3,316,216, issued to Fawcett, et al., on Apr. 25, 1967, discloses the preparation fluorinated dioxolanes of the formula

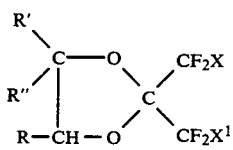

where R, R' and R'' can include H, hydrocarbyl, haloalkyl and various other carbon containing groups, and X and $X^1$ can include H, halogen and perfluoroalkyl, from fluoroketones and epoxides.

U.S. Pat. No. 3,324,144, issued to Coe, et 'al., on June 6, 1967, discloses fluorodioxolanes

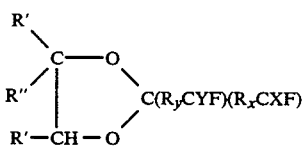

prepared from ketones and epoxides.

U.S. Pat. No. 3,379,736, issued to Dietrich, et al., on April 23, 1968, discloses 4-methylene-1,3-dioxolanes containing either hydrogen and a chlorinated methyl group or a methylene or a chlorinated methylene group in the 2-position.

U.S. Pat. No. 3,450,716, issued to Selman on June 17, 1969, discloses perfluoro-4-oxo-2,5- dimethyl-2-fluorocarbonyl-1,3-dioxolane.

U.S. Pat. No. 3,532,725, issued to Dorfman, et al., on Oct. 6, 1970, discloses the photochlorination of alkyl and aralkyl ester groups of fluorinated esters in the presence of $Cl_2$, UV radiation and, optionally, $CCl°$ as solvent.

U.S. Pat. No. 3,555,100, issued to Garth, et al., on Jan. 12, 1971, discloses the decarbonylation of fluorocarboxylic acid fluorides in the presence of $SbF_5$.

U.S. Pat. No. 3,557,165, issued to Dorfman, et al., on Jan. 19, 1971, discloses the conversion to acyl halides, in the presence of Lewis acids, of fluorinated esters wherein the ester groups contain polyhalogenated alkyl or aralkyl groups. The disclosed Lewis acids include $FeCl_3$, $SbCl_5$, $ZnCl_2$, $ZnCl_4$, $BF_3$, $BCl_3$, $MoCl_5$, tin chlorides and metal chlorides, bromides and iodides such as $ZrI_4$ and antimony bromide.

U.S. Pat. No. 3,749,791, issued to Terrell, et al., on July 31, 1973, discloses halogensubstituted 2,2-bis(trifluoromethyl)-1,3-dioxolanes

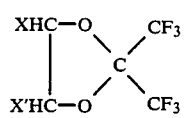

where X is Cl or F and X' is H, Cl, or F, and their preparation by hydrogenation of 2,2-bis(trifluoromethyl)-1,3-dioxolane.

U.S. Pat. Nos. 3,865,845 and 3,978,030, issued to Resnick on Feb. 11, 1975 and Aug. 31, 1976, respectively, disclose fluorinated dioxoles of the formula

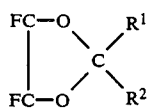

where $R^1$ and $R^2$ are both perhalogenated hydrocarbyl radicals of 1 to 3 carbon atoms containing at least one F atom and preparation of said dioxoles by reacting the corresponding dioxolanes with Mg. The dioxolanes are prepared by fluorination with $SbF_3$-$SbCl_5$ at 120° C. of 2,2-bis-perhaloalkyl)-4,4,5,5-tetrachloro-1,3-dioxolanes, which in turn are prepared from haloketones in accordance with the method described in U.S. Pat. No. 2,925,424.

U.S. Pat. No. 4,182,718, issued to Crutchfield, et al., on Jan. 8, 1980, discloses 1,3-dioxolane and 1,3-dioxane polycarbonates and their precursors having the formula:

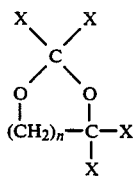

wherein X may be selected from the group consisting of H, $CCl_3$, $CO_2R$, where R is H or lower alkyl, $CO_2M$, where M is alkali metal, $NH_4$ or trialkanolammonium, at least three of the X substituents are other than hydrogen, and n is 1 or 2. The compounds are prepared by the reaction of a halogenated alcohol with a reactive carbonyl to form a halogenated hemi-ketal, followed by reaction with a base to effect cyclization.

U.S. Pat. No. 4,287,124, issued to Siegemund, et al., on Sep. 1, 1981, discloses the preparation of dioxolanes of the formula

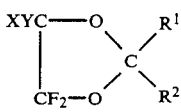

wherein X and Y, independently, are F or $CF_3$ and $R^1$ and $R^2$ are H or $CH_3$, by reacting certain acyl halides with a metal fluoride or ammonium fluoride.

U.S. Pat. No. 4,393,227, issued to Squi July 12, 1983, discloses a process for dechlorinatinq organic compounds having vicinal chlorine atoms, in particular the preparation of dioxoles from dioxolanes as follows:

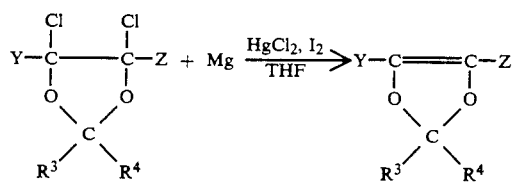

$+MgCl_2$, where each of Y and Z independently is H, Cl or F, and each of $R^3$ and $R^4$ independently is H, F or trifluoromethyl.

U.S. Pat. No. 4,399,264, issued to Squire on Aug. 16, 1983, discloses perfluoro-1,3-dioxole, homopolymers and copolymers thereof, and a process for making the dioxole.

U.S. Pat. No. 4,431,786, issued to Squire on Feb. 14, 1984, discloses fluorodioxoles of the formula

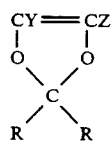

in which Y is hydrogen or chlorine; Z is hydrogen, fluorine, or chlorine; and R is fluorine or the trifluoromethyl group; with the proviso that when R trifluoromethyl, only one of Y and Z can be hydrogen or chlorine. The patent also discloses polymer and copolymers of these dioxoles.

U.S. Pat. Nos. 4,429,143 and 4,496,750, issued to Anderson, et al., on January 31, 1984 and January 29, 1985, respectively, disclose halogenated dioxolanes of the formula:

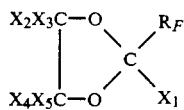

wherein $X_1$ is Cl, F, COF, COCl, $CO_2CCl_3$, $CO_2R$ or $CO_2M$; R is H or alkyl of 1 to 4 carbon atoms; M is an alkali metal ion or ammonium ion; $R_F$ is a perfluoroalkyl group of 1 to 4 carbon atoms; $X_2$, $X_3$, $X_4$ and $X_5$, independently are H, Cl or F; with the proviso that when $X_2$, $X_3$, $X_4$, and $X_5$ are each H, $X_1$ is $CO_2R$ or $CO_2M$. The patents also discloses perhalogenated dioxoles of the formula:

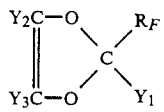

wherein $Y_1$, $Y_2$ and $Y_3$, independently are F or Cl. The patents also disclose homopolymers, copolymers of the dioxoles and methods of making the compounds.

Simmons, et al., Journal of the American Chemical Society 82, 2288 (1960), disclose the preparation of dioxolanes and substituted dioxolanes and specifically mentions that 1,3-dioxolanes were obtained from hexafluoroacetone, sym-difluorotetrachloroacetone and trifluoroacetaldehyde. The general method disclosed for preparing the dioxolanes is the reaction of the appropriate carbonyl compound with an appropriately substituted ethylene halohydrin.

SUMMARY OF THE INVENTION

The present invention provides dioxolanes of the formula

wherein:

$X^1$, $X^2$, $X^3$ and $X^4$ are each —H; each —Cl; or independently —Cl or —F with at least one being —F, and at least one of $X^1$ and $X^2$, and at least one of $X^3$ and $X^4$ being —Cl;

$R^2_F$ is —$R_F$, —H, —Cl, —F or —C(0)Y';

$R_F$ is a perfluorinated linear or branched alkyl group having 1 to 14 carbon atoms and terminally substituted with —F, —Cl, Br, —OR, —$OC_6F_5$, —SR', —$SO_2R'$, —$SO_2F$, —$N_3$, —CN, —COOR', —$OCCl_3$, —SCl, —$SO_2Cl$, —C(O)$OCCl_3$, —C(O)Cl or —C(O)F, or said perfluorinated alkyl group also containing ether oxygen;

R' is an alkyl group of 1 to 4 carbon atoms; Y' is —$OCH_2CH_2X$ wherein X is Cl or Br;

R is an alkyl group of 1 to 4 carbon atoms, —$CH_2CF_3$ or —$C_6H_5$;

$Y^4$ is —$R'_FQ$, —$R^2_F$, —$R'_FC(O)CF_3$, —$OCCl_3$ or OR with $R'_F$ being a single bond or a perfluoroalkylene group of 1 to 4 carbon atoms, or said perfluoroalkylene group containing ether oxygen;

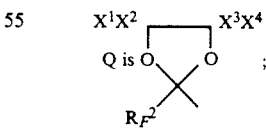

with the provisos that:

(i) when $X^1$, $X^2$, $X^3$ and $X^4$ are each H:

(a) $R^2_F$ is other than —Cl or —F, $Y^4$ is other than —$OCCl_3$ or —$R^2_F$ where —$R^2_F$ is —C(O)Y' and $R_F$ is a perfluorinated alkyl group terminally substituted with —F, —Cl, —OR, —$OC_6F_5$, —SR', —$SO_2R'$, —$SO_2F$, —$N_3$, —CN or —COOR', or said perfluorinated alkyl group also containing ether oxygen;

(b) when $R^2_F$ is —H or —C(O)Y', $Y^4$ is $R_F$ where $R_F$ is perfluoroethyl terminally substituted with —F, —N₃, —OC₆F₅ or —SR'; and (c) when $R^2_F$ is $R_F$ having terminal substitution with —F or —Cl, then $Y^4$ is other than —H, —OR or —$R_F$ having terminal substitution with —F or —Cl;

(ii) when $X^1$, $X^2$, $X^3$ and $X^4$ are each —Cl:

(a) $R^2_F$ is other than —H, —C(O)Y' or —F, $Y^4$ is other than —OR, and $R_F$ has terminal substitution by other than —OR, —SR', —SO₂R', —N₃, —COOR', or —C(O)F;

(b) when $R^2_F$ is $R_F$ having terminal substitution with —F or —Cl, $Y^4$ is other than —Cl or —$R^2_F$ having terminal substitution with —F or —Cl; and (c) when $R^2_F$ is —Cl, $Y^4$ is —$R'_F Q$;

(iii) when $X^1$, $X^2$, $X^3$ and $X^4$ are each —Cl or —F with at least one being —F, and at least one of $X^1$ and $X^2$ and at least one of $X^3$ and $X^4$ being —Cl:

(a) $R^2_F$ is other than —H, —C(O)Y' or —cl, $Y^4$ is other than —OCCl₃ or —OR, and $R_F$ has terminal substitution with —F, —Cl, —OC₆F₅, —SO₂F, —CN, —SO₂Cl, —C(O)Cl or —C(O)F;

(b) when $R^2_F$ is $R_F$ having terminal substitution with —F or —Cl, $Y^4$ is other than —F or —$R^2_F$ having terminal substitution with —F or —Cl; and (c) when $R^2_F$ is —F, $Y^4$ is —$R'_F Q$.

The invention also provides a dioxole of the formula

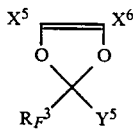

(II)

wherein $X^5$ and $X^6$ are independently —F or —Cl with at least one being —F;

$R^3_F$ is —F, a perfluorinated linear or branched alkyl group having 1 to 14 carbon atoms and terminally substituted with —F, —Cl, —OC₆F₅, —SO₂Cl, —SO₂F, —CN, —C(O)F or —C(0)OR", or said perfluorinated alkyl group also containing ether oxygen;

R" is —CH₃, —C₂H₅ or —CH₂CF₃; $Y^5$ is —F, —$R'_F Q'$, —$R^3_F$ or —$R'_F C(O)CF_3$;

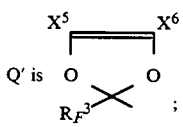

$R'_F$ is a single bond or a perfluorinated alkyl group having 1 to 4 carbon atoms or said group containing ether oxygen;

with the provisos that:

(a) when $R^3_F$ is a perfluorinated alkyl group terminally substituted with —F or —Cl, $Y^5$ is other than —F or —$R^3_F$ having terminal substitution with —F or —Cl; and (b) when $R^3_F$ is —F, $Y^5$ is —$R'_F Q'$.

Also provided are processes for preparing the dioxolanes and homopolymers and copolymers made from the dioxoles.

DETAILED DESCRIPTION OF THE INVENTION

The dioxolanes and dioxoles of the invention have the formulas set forth earlier herein. For the dioxolanes of the invention, preferred embodiments are as follows:

(a) when $X^1$, $X^2$, $X^3$ and $X^4$ are each hydrogen:

$R^2_F$ is —$R_F$, preferably having 1 or 2 carbon atoms and terminal substituents other than —F or —Cl, the substituents most preferably being —CN, —SR', —SO₂F, —OC₆F₅ or —C(O)OCH₃; and $Y^4$ is —H, —OCH₃, —CF₃ or —C₂F₅;

(b) when $X^1$, $X^2$, $X^3$ and $X^4$ are each —Cl:

$R^2_F$ is perfluorinated alkyl, preferably having 1 or 2 carbon atoms and terminal substituents other than —F or —Cl, the substituents most preferably being —CN, —C(O)Cl, —C(O)OCCl₃, —SO₂Cl, —SO₂F or —OC₆F₅;

$Y^4$ is —Cl, —OCCl₃, —CF₃ or —C₂F₅; and (c) when $X^1$, $X^2$, $X^3$ and $X^4$ are each —Cl or —F with at least one being —F, and at least one of $X^1$ and $X^2$ at least one of $X^3$ and $X^4$ being Cl:

$R^2_F$ is perfluorinated alkyl, preferably having 1 or 2 carbon atoms and terminal substituents other than —F or —Cl, the substituents most preferably being —C(O)Cl, —C(O)F, —CN, —SO₂F or —OC₆F₅; and $Y^4$ is —F, —CF₃ or —C₂F₅.

Preferred dioxoles of the invention are those where $X^5$ and $X^6$ are each —F; $R^3_F$ is perfluorinated alkyl, preferably having 1 or 2 carbon atoms and terminal substituents other than —F or —Cl, the substituents most preferably being —CN, —C(O)F, —C(O)OCH₃, —SO₂F or —OC₆F₅; and $Y^5$ is —F, —CF₃ or —C₂F₅.

Dioxolanes of formula I wherein $X^1$, $X^2$, $X^3$ and $X^4$ are —H, $R^2_F$ is —$R_F$, —$R_F$ is perfluorinated alkyl, and $Y^4$ is —H, —OR or —CF₂CF₂Z where Z is —F, —N₃, —OC₆H₅, —SR' or —OC₆F₅, and R' is an alkyl group of 1–4 carbon atoms, are prepared by reacting a -chloro- or 2-bromoethyl ester of the appropriate fluoroalkylcarboxylic acid, said ester having the formula $R_F CO_2 CH_2 CH_2 X$ werein X and R, are as previously defined herein, with a compound of the formula $MY^1$ in a suitable solvent. $Y^1$ is equal to —H, —OR or —CF₂CF₂Z where R and Z are as previously defined herein; and M is Na, Li, K or NR'₄ with R' being an alkyl group of 1–4 carbon atoms. The process can be described by the following equations:

$R_F C(O)Y' + MY^1 \rightarrow QY^1$ (1)

where Y is other than —OR with R being an alkyl group of 1–4 carbon atoms and the other symbols are as previously defined, and

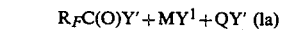

$R_F C(O)Y' + MY^1 + QY'$ (1a)

where $Y^1$ is —OR with R being an alkyl group of 1–4 carbon atoms and the other symbols are as previously defined. The relative amounts of the two products in equation (1a) are determined by the relative amounts of the two starting materials and the basicity of the —OR group with the $QY^1$ product always being the major product. The process is conducted at a temperature of from about −20° to 80° C., preferably from about 0° to about 50° C. Reaction time can vary from a few minutes to several weeks, depending upon reactant and solvent. A pressure of about 101 kPa (14.7 psi) is preferred, but pressure can be from about 6.9 to about 6900 kPa, particularly when tetrafluoroethylene is a reactant, i.e., tetrafluoroethylene is used to prepare $MCF_2CF_2Z$ which serves as $MY^1$ is the reaction above Solvents suitable for this process are dipolar aprotic materials such as dimethyl sulfoxide, diglyme, tetrahydrofuran, dimethylformamide, and the like but dimethyl sulfoxide is preferred. The reactants are generally present in equivalent amounts, but the ratio of equivalents can be varied to promote efficient utilization of the more expensive reactant. The resulting product can be isolated by filtration followed by distillation or crystallization; or by dilution of the resulting reaction mixture with water and subsequent purification of the water insoluble product.

Dioxolanes of the foregoing class wherein $Y^1$ is —OR and R is an alkyl group of 1–4 carbon atoms, can also be prepared by reacting the perfluoroalkylacid ester, $R_FCO_2R$ with a compound of the formula $MOCH,CH,X$ where M and X are as previously defined. This process is described by the following equation:

$$R_FCO_2R + MY^1 \rightarrow QOR + QY^1 \qquad (2)$$

The process conditions and suitable solvents are the same as those prescribed for reactions (1) and (1a). This process is preferred for making QOR dioxolanes because the relative amount of the primary product is greater for this process than for the process of equation 1(a).

The invention also provides a process for preparing dioxolanes of the formula

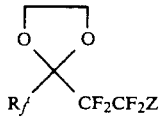

wherein: $R'_f$ is —H, —C(O)Y' or Q'; Y' is —$OCH_2CH_2X$ where X is —Cl or —Br;

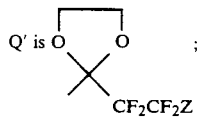

Z is —F, —$N_3$, —$OC_6H_5$, —SR' or $OC_6F_5$; and
R' is an alkyl group of 1 to 4 carbon atoms.
The process comprises reacting (a) 2-chloro- or -bromoethylformate or (b) bis(2-chloroethyl) oxalate or bis(2-bromoethyl) oxalate with a compound of the formula $MCF_2CF_2Z$ in a suitable solvent. The process can be described by the following equations:

$$HC)OY' + MY'' \rightarrow Q'H \qquad (3)$$

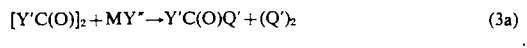

wherein Y'' is $CF_2CF_2Z$. The process can be conducted in a suitable solvent at a temperature of from about $-20°$ to $80°$ C., preferably from about $0°$ to about $50°$ C Pressure can vary over the same range as for reaction (1). The pressure can be from about 6.9 kPa when tetrafluoroethylene is used as a reactant to prepare $MCF_2CF_2Z$. Elevated pressures, from about 6.9 kPa to about 6900 kPa are preferred. Suitable solvents and other reaction conditions are similar to those for reactions (1) and 1(a). Ether solvents are preferred. Process (3) provides preparation of dioxolanes of the invention wherein $X^1, X^2, X^3$ and $X^4$ are each hydrogen; $R^2_F$ is —H, —C(O)Y' or —$CF_2CF_2Z$; and Y' is (a) $R'_FQ$ where $R'_F$ is a single bond or (b) $R^2_F$ where $R^2_F$ is —$R_F$ and $R_F$ is —$CF_2CF_2Z$, provided that either $R^2F$ or $Y^4$ is —$CF_2CF_2Z$.

Dioxolanes of the invention wherein $X^1, X^2, X^3$, and $X^4$ are each —H, $Y^4$ is —OR, $R_F$, $R'_FC(O)R_F$, or $R'_FQ$ and Q is

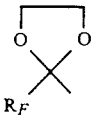

are prepared by reacting in a suitable solvent a compound of the formula $R_FC(O)Y^2$ with a compound of the formula $MY^3$ to produce a compound having the formula $R_FC(OM)Y^2Y^3$ which is then reacted with 2-chloroethanol or 2-bromoethanol to produce the desired dioxolane. In the foregoing formulas for this process (4), $Y^2$ and $Y^3$ are the independently —OR, $R_F$, $R'_F,C(O)CF_3$, or $R'_FQ$, provided that at least one of $Y^2$ and $Y^3$ is —OR. The other symbols are as previously defined. The process can be described by the following equation (4):

$$R_FC(O)Y^2 + MY^3 \longrightarrow R_FC(O)MY^2Y^3 \xrightarrow{HOCH_2CH_2X}$$

$$QY^6 + MX + ROH$$

In equation (4) $Y^6$ is equal to $Y^2$ or $Y^3$ depending upon which of $Y^2$ or $Y^3$ is —OR. The process is conducted at a temperature of from about $-20°$ C. to about $80°$ C., preferably from about $0°$ C. to about $50°$ C. Suitable solvents include pentane, ether and dimethylsulfoxide. Other process conditions are the same as those prescribed for reactions (1) and (1a).

The dioxolanes of formula I wherein $X^1, X^2, X^3$ and $X^4$ are each Cl or are independently Cl or F with at least one being F and at least one of $X^1$ and $X^2$ and at least one of $X^3$ and $X^4$ being Cl can be prepared from the corresponding dioxolanes of formula I wherein $X^1$ to $X^4$ are each —H by known processes, particularly those described in U.S. Pat. Nos. 4,429,143 and 4,496,750 issued to Anderson et al., 4,393,227 and 4,399,264 issued to Squire, and 3,865,845 and 3,978,030 issued to Resnick.

The dioxoles of the invention can be prepared by known processes described in the aforementioned patents.

The dioxoles of the invention can be homopolymerized, or copolymerized with one or more polyhalogenated vinyl monomers of the formula $$CZ^1Z^2 = CF_2$$

wherein $Z^1$ is H, F or Cl; $Z^2$ is H, F, Cl or $OR_H$; $R_H$ is perhaloalkyl of 1 to 4 carbon atoms, $-(-CF-)_n-CF=CF_2$, or $-(-CF_2CF(CF_3)O-)_n-CF_2CF_2Z$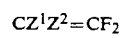; n is an integer from 0 to 6; $Z^3$ is $SO_2F$, $CO_2R^6$ is H or an alkyl group of 1 to 4 carbon atoms. They can also be copolymerized with perfluoro-2,2-bis(methyl)-1,3-dioxole. Tetrafluoroethylene, chlorotrifluoroethylene, perfluoromethylvinyl ether and perfluoropropylvinyl ether are preferred comonomers. Polymers of the invention will generally contain about 0.5 to 100 mol percent of units derived from monomers of the invention.

The polymers are prepared by well-known free-radical techniques, particularly those employed for copolymerization of tetrafluoroethylene which are described in the literature. Preferably, polymerization is conducted in nonaqueous media in a perfluorinated or fluorine-containing perhalogenated solvent, such as perfluorodimethylcyclobutane or 1,1,2-trichlorotrifluoroethane and the like. Useful free-radical initiators include a perfluorocarbon peroxide such as perfluoropropionyl peroxide or an azo compound such as azo-bis-(isobutyronitrile). Polymerization can be conducted at a temperature of from about 0° C to about 200° C, preferably from about 20° C to about 80° C, and at a pressure of from less than about 101 kPa to about 0.02 MPa. The polymers of the invention are expected to have increased Tg's. The dioxoles of the invention in conferring higher Tg's lead to higher service (use) temperatures in the copolymers made therefrom. The dioxoles of the invention contain functional groups which allow crosslinking and other chemical modifications of polymers made therefrom. This enables the polymer to be converted to conductive membranes or ion exchange materials of high stability.

The invention is further illustrated by the following examples in which percentages and ratios are by weight and temperatures are in degrees Celsius unless otherwise stated. The dioxolanes illustrated in the examples are listed in Tables 1-3. The compounds are coded in the examples pursuant to the numbers specified in Tables. For all the dioxolanes in Examples 1-17, $X^1$, $X^2$, $X^3$ and $X^4$ are H (Table 1). For the dioxolanes in Examples 18, 19, 21, 22 and 24, $X^1$ to $X^4$ are each —Cl. For the dioxolanes in Table 3 $X^1$—$X^4$ are —F or —Cl with at least one being —F. For all these dioxolanes $X^2$ and $X^3$ were considered to be —Cl and $X^4$ to be —F. the examples having an asterisk beside them indicate examples which illustrate a process of the invention only with the products being outside of the present invention.

TABLE 1

| Example | Process | $R^2_F$ | $Y^4$ | Compound Code |
|---|---|---|---|---|
| 1(a)* | 1(a) | $CF_3$ | $OCH_3$ | 1 |
| 1(a)* | 1(a) | $CF_3$ | $OCH_2CH_2Cl$ | 2 |
| 1(b)* | 2 | $CF_3$ | $OCH_3$ | 1 |
| 1(b)* | 2 | $CF_3$ | $OCH_2CH_2Cl$ | 2 |
| 2* | 1(a) | $F(CF_2)_7$ | $OCH_3$ | 3 |
| 2* | 1(a) | $F(CF_2)_7$ | $OCH_2CH_2Cl$ | 4 |
| 3* | 1 | $CF_3$ | H | 5 |
| 4* | 1 | $CF_3$ | $OC_6H_5$ | 6 |
| 5 | 1 | $CF_3$ | $C_6H_5OCF_2CF_2$ | 7 |
| 6 | 3 | H | $C_6H_5OCF_2CF_2$ | 8 |
| 7 | 3(a) | Q' | $C_6H_5OCF_2CF_2$ | 9 |
| 7 | 3(a) | $CO_2CH_2CH_2Cl$ | $C_6H_5OCF_2CF_2$ | 10 |
| 8(a) | 1 | $CF_3$ | $N_3CF_2CF_2$ | 11 |
| 8(b) | 4 | $CF_3$ | $N_3CF_2CF_2$ | 11 |
| 8(b) | 4 | $CF_3$ | $CNCF_2$ | 12 |
| 9(a) | 2 | $CH_3OCF_2CF_2$ | $OCH_3$ | 13 |
| 9(a) | 2 | $CH_3OCF_2CF_2$ | $OCH_2CH_2Cl$ | 14 |
| 9(b) | 4 | $CH_3OCF_2CF_2$ | $OCH_3$ | 13 |
| 10 | 2 | $CH_3O_2CCF_2CF_2$ | $OCH_3$ | 15 |
| 10 | 2 | $CH_3O_2CCF_2CF_2$ | $OCH_2CH_2Cl$ | 16 |
| 11 | 2 | $CNCF_2$ | $OCH_3$ | 17 |
| 11 | 2 | $CNCF_2$ | $OCH_2CH_2Cl$ | 18 |

TABLE 1-continued

| Example | Process | $R^2_F$ | $Y^4$ | Compound Code |
|---|---|---|---|---|
| 12 | 4 | $CH_3O_2CCF_2$ | $CH_3O_2CCF_2$ | 19 |
| 13 | 4 | $CNCF_2$ | $CF_3$ | 20 |
| 13 | 4 | $N_3CF_2CF_2$ | $CF_3$ | 20a |
| 14 | 4 | $CF_3$ | Q | 21 |
| 14 | 4 | $CF_3$ | $C(O)CF_3$ | 22 |
| 15 | | $CH_3OCF_2CF_2$ | $CH_3OCF_2CF_2$ | 23 |
| 16 | | $CF_3$ | $CF_2OCF(CF_3)$-$CO_2CH_3$ | 24 |
| 17* | 1 | $CF_3$ | $CF_2CF_3$ | 25 |

TABLE 2

| Example | Source of Starting Dioxolane | $R^2_F$ | $Y^4$ | Compound Code |
|---|---|---|---|---|
| 18 | Ex. 1(b) | $CF_3$ | $OCCl_3$ | 26 |
| 18 | Ex. 1(b) | Cl | $CF_3$ | 27 |
| 19 | Ex. 10 | $Cl_3CO(O)C$—$CF_2CF_2$ | Cl | 28 |
| 21 | | | $Cl_3COCF_2CF_2$ | $CF_2CF_2OCCl_3$ | 31 |
| 22 | Ex. 9 | $Cl_3COCF_2CF_2$ | Cl | 32 |
| 24 | Ex. 8(b) | $CF_2CN$ | $CF_3$ | 33 |

TABLE 3

| Example | Source of Starting Dioxolane | $R_2F$ | $Y^4$ | Compound Code |
|---|---|---|---|---|
| 20 | Ex. 19 | $F(O)CCF_2CF_2$ | F | 29a |
| 20 | Ex. 19 | $Cl(O)CCF_2CF_2$ | F | 30a |
| 20 | Ex. 19 | $Cl(O)CCF_2CF_2$ | F | 29b |
| 20 | Ex. 19 | $CH_3O(O)CCF_2CF_2$ | F | 29 |
| 20 | Ex. 19 | $CH_3O(O)CCF_2CF_2$ | F | 30 |
| 25 | Ex. 24 | $CF_2CN$ | $CF_3$ | 34 |
| 25 | Ex. 24 | $CF_2CN$ | $CF_3$ | 35 |

EXAMPLE 1

2-Methoxy-2-trifluoromethyl-1,3-dioxolane (1) and 2-(2-chloroethoxy) -2-trifluoromethyl -1,3-dioxolane (2)

This Example illustrates a process of the invention only.

A. 2-Chloroethyl trifluoroacetate, b.p. 66°-68° at 20 kPa (150 mm) was prepared in 81% yield by the addition of one equivalent of pyridine to a mixture of one equivalent each of trifluoroacetyl chloride and 2-chloroethanol in ether solution. The product was isolated by filtration and distillation of the filtrate.

Anal. Calcd. for $C_4H_4ClF_3O_2$: C, 27.21; H, 2.28; Found: C, 27.74; H, 2.54

2-Chloroethyl trifluoroacetate can be more conveniently prepared by reaction of equimolar amounts of trifluoroacetic acid and 2-chloroethanol at 25° in the presence of concentrated sulfuric acid for one day followed by distillation.

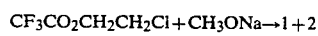

A suspension of 5.4 g (0.10 mol) of sodium methoxide in 50 mL of tetrahydrofuran (THF) was stirred at −20° to −10° while 17.7 g (0.10 mol) of 2-chloroethyl trifluoroacetate were added dropwise. The resulting clear solution was allowed to warm with precipitation commencing at about 10° and a slow exotherm ensuing to 35° . The mixture was maintain below 35° until the exotherm subsided and then was stirred for 4 h. Filtration and fractionation of the filtrate gave 7.4 g (43% yield) of 2-methoxy-2-trifluoromethyl-1,3-dioxolane, b.p. 61°-62° at 3.3 kPa (25 mm). IR (neat): 3000, 2965, 3 2925, and 2680 (sat,d CH), 1250-1100 cm$^{-1}$(CF, C—O). NMR (CCl$_4$): $^1$H 4.17 (m, 4H, ring CH$_2$ and 3.33 ppm (s, 3H, OCH$_3$);$^{19}$F-85.0 ppm (s, CF$_3$).

Anal.: Calcd. for C° H'F'O ' C, 34.89; H, 4.10. Found: C, 34.88; H, 3.94

Further fractionation of the filtrate gave 1.6 g (14% yield based on the ester) of 2-(2-chloroethoxy)-2-trifluoromethyl-1,3-dioxolane, b.p. 103°-104° at 3.3 kPa (25 mm). IR (neat): 2985 and 2930 (sat'd CH), 1250-1000 cm$^{-1}$(CF, C—O). NMR (CCl$_4$):$^1$H 4.20 (m, 4H, ring CH$_2$), 3.81 (m, 2H, CH$_2$), and 3.62 ppm (m, 2H, CH$_2$);$^{19}$F-84.9 (s, CF$_3$).

Anal Calcd for C$_6$H$_8$ClF$_3$O: C, 32.67; H, 3.65; Cl, 16.08. Found: C, 32.79; H, 3.45; Cl, 15.92.

B. CF$_3$CO$_2$CH$_3$+ClCH$_2$CH$_2$OH +NaH →1 +2

A mixture of 42.0 g (0.33 mol) of methyl trifluoroacetate, 26.6 g (0.33 mol) of -chloroethanol, and 150 mL of dimethylsulfoxide (DMSO) was stirred at 10°-20° while 15.8 g (0.33 mol) of 50% NaH in mineral oil was added portionwise. The resulting mixture was stirred at 20° for 2 h, at 25° for several days, and then poured into 1 L of water. The resulting aqueous layer was extracted with 100 mL of ether. The organic layers were combined, then washed twice with water, dried over CaSO$_4$, and distilled to give 35.6 g (63% yield) of 2-methoxy-2-trifluoromethyl-1,3-dioxolane, b.p. 60°-65° at 3.3 kPa (25 mm), and a residue containing about 4.8 g (7% yield) of by-product -(2-chloroethoxy)-2-trifluoromethyl-1,3-dioxolane (estimated by GC).

EXAMPLE 2

2-Methoxy-2-perfluoro-n-heptyl-1,3-dioxolane (3) and (2-Chloroethoxy)-2-perfluoro n-heptyl 1,3-dioxolane

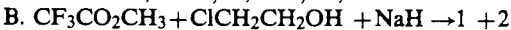

F(CF$_2$)$_7$CO$_2$CH$_2$Cl+CH$_3$ONa→3+4

2-Chloroethyl perfluorooctanoate was prepared by adding 162 g (0.375 mol) of perfluorooctanoyl chloride to 32.2 g (0.40 mol) of 2-chloroethanol cooled at 0° C, stirring the resulting mixture at 0° for 2 h, and then stirring for about 2.5 days at 25°. Fractionation of the resulting solution gave 152.6 g (85% yield) of the chloroethyl ester, b.p. 84°-88° at 1.3 kPa (10 mm), 98% pure by GC. IR (CCl$_4$): 2960 (sat'd CH), 1790 (C=O), 1300—1100 cm$^{-1}$(CF, C—O). NMR (CCl$_4$) :$^1$H 4.59 (t, J$_{HH}$5.5 Hz, 2H, CH$_2$) and 3.70 ppm (t, J$_{HH}$5 Hz, 2H, CH$_2$); $^{19}$F-81.6(t of t, J$_{FF}$10,4Hz, 3F, CF$_3$), −119.0 (t of t, J$_{FF}$ 12, 6 Hz, 2, F, CF$_2$C=O),−122.4 (m, 4F, CF$_2$), −123.3 (m, 4F, CF$_2$), and −126 8 ppm (m, 2F, CF$_2$).

2-Chloroethyl perfluorooctanoate (47.7 g, 0.10 mol) was added at 20° to a suspension of 4.8 g (0.10 mol) of 50% NaH in mineral oil in 100 mL of dry DMSO, and 50 mL of diglyme were added. The resulting mixture was cooled to 10°; 3.2 g (0.10 mol) of methanol were added; and the resulting mixture was warmed Evolution of gas commenced and became brisk. Cooling was required to keep the reaction temperature below 30°. The reaction mixture was stirred overnight and then poured into 500 mL of cold water, thereby causing a separation into layers. The lower layer was washed with 200 mL of water, dried and distilled to give 11.4 g (27% yield) of by-product methyl perfluorooctanoate, b.p. 61°-70° at 2.7 kPa (20 mm); identified by IR and NMR spectra. Further fractionation gave 13.0 g (28% yield) of crude 2-methoxy-2-perfluoro--heptyl-1,3-dioxolane (3), b.p. 75°-84° at 0.35 kPa (2.6 mm). A pure fraction, b.p. 79° at 2.6 mm, was analyzed. IR (neat): 3000, 2960, 2920, and 2860 (sat'd CH), 1250-1100 cm$^{-1}$ (CF, C—O). NMR (CCl$_4$): $^1$H 4.20 (s, 4H, ring OCH$_2$) and 3.36 ppm (s, 3H, )CH$_3$);$^{19}$F -81.6 (t of m, J$_{FF}$ 9.5 Hz, 3F, CF$_3$), −122.0 (m, 2F, CF,), −122.6 (m, 4F, CF$_2$), -123.3 (m, 4F, CF$_2$), and -126.8 ppm (m, 2F, CF$_2$).

Anal.: Calcd. for C$_{11}$ H$_7$F$_{15}$O$_3$: C, 27.98, H, 1.50; F, 60.36; Found: C, 28.28; H, 1.56; F, 61.11.

2-Chloroethoxy-2-perfluoro-n-heptyl-1,3dioxolane (4) was also obtained, b.p. 70°-72.5° at 27 Pa (0.2 mm), 3 5 g (7% yield). IR (neat): 2980 and 2920 (sat'd CH) and 1300-1100 cm$^{-1}$ (CF, C—O). NMR (CCl$_4$): 'H 4.23 (s, 4H, ring OCH$_2$), and 3.87 and 3.57 ppm (AA'BB'm, 4H, CH$_2$); $^{19}$F -81 6 (t of m, J$_{FF}$10 Hz, 3F, CF$_3$), −121.8 (m, 2F, CF,), −122.5 (m, 4F, CF$_2$), -123.2 (m, 4F, CF$_2$, and -126.8 ppm (m, 2F, CF$_2$).

Anal.: Calcd. for C H:ClF >0.: C, 27.68; H, 1.55; Cl, 6.81. Found: C, 28.32; H, 1.69; Cl, 6.87.

EXAMPLE 3

2 Trifluoromethyl-1,3-dioxolane (5)

This example illustrates a process of the invention only. A suspension of 9.6 g (0.20 mol) of 50% NaH in mineral oil in 150 mL of DM$0 was stirred at 15°-20° while 35.4 g (0.20 mol) of 2-chloroethyl trifluoroacetate were added dropwise. The resulting mixture was stirred overnight while the reaction temperature was maintained below 30°. The reaction mixture was then heated to 50° at 0.33 kPa (2.5 mm) to drive off volatile products which were recovered. Fractionation of the volatiles gave 8.5 g (30% yield) of 2-trifluoromethyl-1,3-dioxolane, b.p. 87°-93°. IR (CCl$_4$): 3000 and 2910 (sat'd CH), 1200-1100 cm$^{-1}$ (CF,C—O). NMR (CCl$_4$): $^1$H 5.13 (q, J$_{HF}$ 4Hz, IH, CH) and 4.07 ppm (s, 4H, ring OCH$_2$). Anal.: Calcd. for C$_4$H$_5$F$_3$O$_2$: C, 33.81; H, 3.55. Found: C, 33.68; H, 3.39

EXAMPLE 4

2-Phenoxy-2-trifluoromethyl-1,3-doxolane (6)

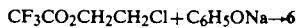

CF$_3$CO$_2$CH$_2$CH$_2$Cl+C$_6$H$_5$ONa→6

A solution of 23.5 g (0.25 mol) of phenol in 50 mL of DMSO was added dropwise to a stirred suspension of 12.0 g (0.25 mol) of 50% NaH in mineral oil in 100 mL of DMSO maintained at 15°-20° by cooling. After evolution of gas had slowed, cooling and stirring were continued while 44.3 g (0.25 mol) of 2-chloroethyl trifluoroacetate were added. The temperature of the reaction mixture was kept below 30° while the exotherm which occurred subsided, then the resulting mixture was stirred overnight, poured into 1 L of water, and extracted with 200 mL, then two 100 mL portions, of ether. The resulting ether solutions were washed with water, dried over CaSO$_4$, and distilled to give 27.6 g (47% yield) of 2-phenoxy-2-trifluoromethyl-1,3-dioxolane, b.p. 52°-54° at 80 Pa (0.6 mm). IR (neat) and NMR (CCl$_4$) spectra were consistent with the assigned structure.

Anal.: Calcd. for C$_{10}$H$_9$F$_3$O$_3$: C, 51.29; H, 3.87; F, 24.34. Found: C, 51.19; H, 3.92; F, 24.49.

EXAMPLE 5

2-Trifluoromethyl-2-(2-phenoxytetrafluoroethyl)1,3-dioxolane (7)

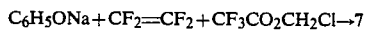

$C_6H_5ONa + CF_2{=}CF_2 + CF_3CO_2CH_2CH_2Cl \rightarrow 7$

A suspension of 12.0 g (0.25 mol) of 50 % NaH in mineral oil in 100 mL of dry diglyme (diethylene glycol dimethyl ether) was stirred at 25° under nitrogen while a solution of 23.5 g (0.25 mol) of phenol in 50 mL of diglyme was added. The resulting mixture was stirred until evolution of gas ceased, then charged into a 400 mL metal tube along with 44.3 g (0.25 mol) of 2-chloroethyl trifluoroacetate and 40 g (0.70 mol) of tetrafluoroethylene. The resulting mixture was agitated for 6 h while the temperature rose to 34° and subsided. Next the mixture was heated at 50 ° for 6 h. The resulting reaction mixture was added to L of water, thereby causing the formation of layers. The lower layer was separated, washed with water, dried over $CaSO_4$, and distilled to give 61.2 g (73% yield) of 2-trifluoromethyl-2(2-phenoxytetrafluoroethyl)-1,3-dioxolane, b.p. 64°–67° at 13 Pa (0.1 mm). The IR ($CCl_4$) and NMR (CC14) spectra of the product were consistent with the structure assignment. Anal.: Calcd. for $C_{12}H_9F_7O_3$:C,43.13; H, 2.71; F, 39.80. Found: C, 43.23; H, 2.75; F, 39.90.

EXAMPLE 6

2-(2-phenoxytetrafluoroethyl)-1,3-dioxolane (8)

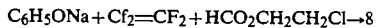

$C_6H_5ONa + Cf_2{=}CF_2 + HCO_2CH_2CH_2Cl \rightarrow 8$

A suspension of 17.3 g (0.36 mol) of 50% NaH in mineral oil in 100 mL of diglyme was treated with a solution of 33.9 g (0.36 mol) of phenol in 50 mL of diglyme. The resulting mixture was stirred overnight and then charged into a 400 mL metal tube along with 38.6 g (0.36 mol) of 2-chloroethyl formate and 40 g (0.40 mol) of tetrafluoroethylene. The resulting mixture was agitated for 12 h, and then added to 1 L of cold water, thereby causing the formation of layers. The lower layer was washed with water, dried over $CaSO_4$, and distilled to afford 54.5 g (57% yield) of 2-(2-phenoxytetrafluoro-ethyl)-1,3-dioxolane, b.p. 62°–65° at 8 Pa (0.06 mm). The IR (neat) and NMR ($CCl_4$) spectra of the product were consistent with the assigned structure. Anal.: Calcd. for $C_{11}H_{10}F_4O_3$:C, 49.63; H, 3.791 F, 28.55. Found: C, 49 90; H, 3.80; F, 28.91.

EXAMPLE 7

2,2'- Bi(2-[2-phenoxytetrafluoroethyl]-1,3-dioxolane) (9) and 2 (2-Phenoxytetrafluoroethyl)-2-(2-chloroethoxy-carbonyl)-1,3-dioxolane (10)

$(ClCH_2CH_2OCO)_2 + C_6H_5ONa + CF_2CF_2 \rightarrow 9 + 10$

Bis(2-chloroethyl) oxalate was prepared by dropwise adding 95.1 g (0.75 mol) of oxalyl chloride to 120.8 (1.50 mol) of 2-chloroethanol maintained at 25°–30° . Reaction of these materials was continued over night. The resulting product was distilled to give 150.0 g (93% yield) of bis(2-chloroethyl) oxalate, b.p. 93°–94° at 27 Pa (0.2 mm), m.p. 41°–42° . The IR ($CCl_4$) and NMR ($CCl_4$) spectra of the product were consistent with the assigned structure.

Anal Calcd. for $C_6H_8Cl_2O_4$: 33.51; H, 3.75; Cl, 32.98. Found: C, 33.51; H, 3.27; Cl, 32.71.

A suspension of 24.0 g (0.50 mol) of 50% NaH in mineral oil in 100 mL of diglyme was treated with a solution of 47.0 g (0.50 mol) of phenol in 50 mL of diglyme. The resulting mixture was stirred overnight, and then charged into a 400 mL metal tube along with 53.8 g (0.25 mol) of bis(2-chloroethyl) oxalate and 50 g (0.50 mol) of tetrafluoroethylene. The resulting reaction mixture was agitated for 12 hr, and then shaken with 1 L of cold water, after which layers formed. The lower layer, which was a mixture of solid and oil, was dissolved in 900 mL of ether to give an ether solution which was dried over $CaSO_4$, filtered, and concentrated to 200 mL. Addition of 50 mL of petroleum ether to the concentrated ether solution caused precipitation of a crystalline product which was filtered off and rinsed to give 59.1 g of crystalline 2,2'-bi(2-[2phenoxytetrafluoroethyl]-1,3-dioxolane), m.p. 102°–103° . The filtrate was cooled to obtain a second crop of crystals, m.p. 92°–97° , to give a total of 64.5 g (49% yield) of the bisketal. An analytical sample , m.p. 102.5°–103.5° , was obtained by recrystallization of some of the product from tetrahydrofuran/ petroleum ether mixed solvent. The IR (KBr) and NMR (acetone-$d_6$) spectra of the product were consistent with the structure. Anal.: Calcd. for $C_{22}H_{18}F_8O_6$: C, 49.82; H, 3.42; F, 28.66. Found: C, 50.02; H, 3.47; F, 28.68.

The filtrate from the second crop of bisketal was evaporated to a heavy residual oil having a mineral oil upper layer which was then removed. The remainder of the material was distilled through a molecular still to afford 21.0 g (23% yield) of 2-(2-phenoxytetrafluoroethyl)-2-(2-chloro-ethoxycarbonyl)-1,3-dioxolane, b.p. 132°–135°(0.06 mm), contaminated with a small amount of mineral oil. An analytical sample was obtained by extraction of some of the product six times with petroleum ether, and then subjecting the combined extract to reduced pressure (13 Pa, 0.1 mm) at 25° , after which GC and $^1H$ NMR indicated that the product was pure. IR (neat) and NMR ($CCl_4$) spectra for the product were consistent with the assigned structure.

Anal : Calcd. for $C_{14}H_{13}ClF_4O_5$:C, 45.12; H, 3.52; Cl, 9.51. Found: C, 45.40; H, 3.52; Cl, 9.21.

EXAMPLE 8

2-(2-Azidotetrafluoroethyl)-2-trifluoromethyl-1,3 dioxolane (11) and 2-Trifluoromethyl 2-cyanodifluoromethyl 1,3 dioxolane (12)

A. $NaN_3 + CF_2{=}CF_2 + CF_3CO_2CH_2CH_2Cl \rightarrow 11$

A 400 mL tube was charged with 16.3 g (0.25 mol) of sodium azide, 44.3 g (0.25 mol) of 2-chloroethyl trifluoroacetate, 150 mL of DMSO, and 40 g (0.40 mol) of tetrafluoroethylene, and then shaken for 8 h. Gases evolving from the reaction mixture were bled off, and the resulting residue was warmed under reduced pressure until only DMSO was being volitilized off. The volatiles were collected and then fractionated to give 20.1 g (45% recovery) of the starting 2-chloroethyl trifluoroacetate, b.p. 37°–39° at 3.3 kPa (25 mm), identified by IR, followed by 22.7 g of crude azide product, b.p. 44°–58° at 0.93 kPa (7.0 mm). This crude product was washed twice with water, dried over $CaSO_4$, and distilled to give 14.8 g (21% conversion, 39% yield) of 2-(2-azidotetrafluoroethyl)-2-trifluoro-methyl-1,3-dioxolane, b.p. 60°–61° at 1.25 kPa (9 mm), GC pure. IR (CCl₄) and NMR and (CCl) spectra of the product were consistent with the assigned structure.

B. N₃CF₂CF₂C(ONa)(OCH₂CF₃)CF₃ + ClCH₂CH₂OH → 11

A 400 mL metal tube was charged with 32.5 g (0.50 mol) of sodium azide, 98.0 (0.50 mol) of trifluoroethyl trifluoroacetate, 150 mL of DMSO, and 50 g (0.50 mol) of tetrafluoroethylene, and then shaken for 6 h without heating and then one h at 40°. A total of three such reactions were run, and the resulting solutions of intermediate salt were combined.

The combined solutions of intermediate salt were stirred at 25°–30° while 129 g (1.6 mol) of 2-chloroethanol were added dropwise. The resulting reaction mixture was stirred for 4 h after the addition had been completed. Another 32 g (0.40 mol) of 2-chloroethanol were added, and the resulting mixture was stirred overnight. Next, the mixture was poured into 1 L of cold water, causing separation into layers. The lower (organic) layer (390 g) was separated. The aqueous layer was extracted with 500 mL of ether, and the combined organic layers were washed with 300 mL of water and dried over CaSO₄. GC analysis indicated that the solution contained 37% of 2-(2-azidotetrafluoroethyl)-2-trifluoromethyl-1,3-dioxolane. The identity of this product was confirmed by adding the ether solution over a period of 1.5 hr to a solution of 393 g (1.5 mol) of triphenylphosphine in 1 L of ether while the triphenylphosphine solution was stirred under a water-cooled condenser. The resulting mixture was stirred an additional 0.5 h, during which time vigorous evolution of N₂ and the accompanying exotherm abated. The mixture was filtered, and the resulting solids were rinsed with ether. The filtrate was concentrated and its volatiles content were collected under reduced pressure and the resulting volatiles were collected and fractionated to give 193 g (59% yield from tetrafluoroethylene) of 2-trifluoromethyl-2-cyanodifluoromethyl-1,3dioxolane (12), b.p. 64°–66° at 6.6 kPa (50 mm).

EXAMPLE 9

2-Methoxy-2-(2-methoxytetrafluoroethyl)-1,3dioxolane (13) and
2-(2-Chloroethoxy)-2-(2-methoxy-tetrafluoroethyl)-1,3 ioxolane (14) -d A. CH₃OCF₂CF₂CO₂CH₃ → ClCH₂CH₂OH + NaH → 13 + 14

A mixture of 95.0 g (0.50 mol) of methyl 3-methoxytetrafluoropropionate, 24 g (0.50 mol) of 50% NaH in mineral oil, and 500 mL of THF was stirred at −20° while 40.3 g (0.50 mol) of 2-chloroethanol were added dropwise The resulting mixture was stirred at −20° while hydrogen evolution (abated in 15 min), and then at about 30° until the ensuing exotherm subsided (about 2-3 h). The mixture was filtered, and solvents were distilled from the resulting filtrate. The residue was added to 700 mL of water, causing separation into layers. The lower layer was dried over anhydrous Na₂CO₃, and distilled to give 30.4 g (32%) of recovered ester, b.p. 30°–32° at 5 3 kPa (40 mm), identified by IR, and 18.0 g of a mixture of products, b.p. 40°–50° at 20 Pa (0.15 mm). Fraction of the mixture of products gave 10.6 g (9% spectrum to that of the product from part A of this Example.

EXAMPLE 10

2 Methoxy-2-(2-methoxycarbonyltetrafluoroethyl) 1,3 dioxolane (15) and 2-(2-chloroethoxy)-2-(2-methoxycarbonyltetrafluoroethyl)-1,3-dioxolane (16)

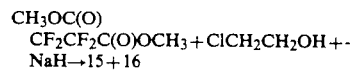

CF₂CF₂C(O)OCH₃ + ClCH₂CH₂OH + NaH → 15 + 16

A mixture of 43.6 g (0.20 mol) of dimethyl tetrafluorosuccinate, 16.1 g (0.20 mol) of 2-chloroethanol, and 100 mL of DM$0 was stirred and maintained at 25°–35° while 9.6 g (0.20 mol) of 50% NaH in mineral oil were added portionwise. The resulting mixture was stirred overnight, and then poured into 500 mL of cold water. Ether (300 mL) was added, and the resulting mixture was shaken. After mixture separated into layers, the ether layer was separated, washed with 100 mL of water, dried over CaSO₄, filtered and distilled to give 23.1 g (44%) of 2-methoxy-2-(2-methoxycarbonyltetrafluoroethyl)1,3-dioxolane, b.p. 72°–72.5° at 13 Pa (0.1 mm). IR (neat) and NMR (CCl₄) spectra of the product were consistent with the assigned structure. Anal.: Calcd for C₈H₁₀F₄O₅:C, 36.65; H, 3.85; F, 28.99. Found: C, 36.45; H, 3.95; F, 28.70.

Further fractionation gave 5.9 g of crude 2-(2-chloroethoxy)-2-(2-methoxycarbonyltetrafluoro-ethyl)-1,3-dioxolane, b.p. 97°–102° at 13 Pa (0.1 mm), which crystallized on standing. The crystals were washed with petroleum ether to give 4.6 g (7% yield) of the product, m.p. 38°–39°. An analytical sample was obtained by recrystallization of a portion of the product from a mixture of ether and petroleum ether, m.p. 38°–39°. IR (CCl₄) and NMR (CCl₄) spectra of the product were consistent with the assigned structure. Anal.: Calcd. for C₉H₁₁ClF₄O₅: amount of mineral oil and then subjecting the material to reduced pressure of 66.5 Pa (0.5 mm) to eliminate residual petroleum ether. IR (neat) and NMR (CCl₄) spectra of the product were consistent with the assigned structure. Anal.: Calcd. for C₇H₈ClF₂NO₃: C, 36.94; H, 3.54; N, 6.15. Found: C, 37.20; H, 3.93; N, 6.41.

EXAMPLE 12

2,2-Bis(methoxycarbonyldifluoromethyl)-1,3- c dioxolane (19)

CH₃OC(O)CF₂C(O)CF₂C(O)OCH₃ +

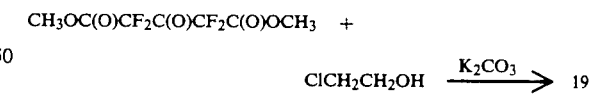

A mixture of 16.5 g (0.25 mol) of dimethyl tetrafluoroacetone-1,3-dicarboxylate, 20.1 g (0.25 mol) of 2-chloroethanol, and 50 mL of pentane was stirred at 20° while 38 g (0.28 mol) of anhydrous were added portionwise over a 15-min period. Next, ether was added and stirring was continued for day. The resulting mixture was filtered, and the resulting filtrate was evaporated to give a mixture of solid and oil. Crystallization of the mixture from 2:1 ether/pentane mixed solvent gave 10.3 g of solid, m.p. 61°–65°. Extraction of the filter cake with 100 mL of ether gave another 4.2 g, m.p. 62°–65°, for a total of 14.5 g of crude product. Recrystallization of the crude product from ether/hexane mixed solvent gave 11.1 g (15% yield) of 2,2-bis(methoxycarbonyldifluoro-methyl)-1,3-dioxolane, m.p. 66.5°–67.5°. A sample sublimed at 60° and 27 Pa (0.2 mm) was analysed. IR KBr) and NMR (acetone-d₆) of the product were consistent with the assigned structure. Anal.: Calcd. for C$_9$H$_{10}$F$_4$O$_6$:C, 37.25; H, 3.47. Found: C, 37.11; H, 3.55.

EXAMPLE 13

2-{2 Azidotetrafluoroethyl)-2-trifluoromethyl)-dioxolane (20a) and 2-trifluoromethyl-2 cyanodifluoromethyl -1,3-dioxolane (20)

A solution of 103.4 g (0.43 mol) of 4-azidoperfluorobutanone-2 in 100 mL of THF was stirred in a container placed in an ice-bath while 40.5 g (0.50 mol) of 2-chloroethanol were added. The resulting mixture was added dropwise to a stirred suspension of 24.0 g (0.50 mol) of 50% NaH in mineral oil in 150 mL of THF while the temperature was maintained at 20°–25° . The mixture was stirred overnight. About 200 mL of solvent was distilled off at b.p. of 32°–36° and 33.25 kPa (250 mm), and the resulting residue was added to 500 mL of water, causing layers to form. The lower layer was separated, dried over CaSO$_4$, filtered and distilled to give 80.6 g (66%) of 2-(2-azidotetrafluoroethyl)2-trifluoromethyl-1,3-dioxolane. b.p. 59°–60° at 1.25 kPa (9.4 mm), and identified by GC and IR.

A solution of 26.3 g (0.10 mol) of triphenylphosphine in 150 mL of ether was stirred while 28.3 g (0.10 mol) of the azidodioxolane prepared pursuant to the foregoing paragraph were added rapidly. A mild exotherm ensued and was accompanied by gas evolution and yellowing. The resulting mixture was stirred for 4 days, filtered and distilled to give 19.7 g (91% yield) of 2-trifluoromethyl-2-cyanodifluoromethyl-1,3-dioxolane, b.p. 67°–68.5° at 6.65 kPa (50 mm). IR (neat) and NMR (CCl$_4$) spectra for the product were consistent with the assigned structure. Anal.: Calcd. for C$_4$H$_4$F$_5$NO$_2$: C, 33.20; H, 1.86; N, 6.45. Found: C, 33.68; H, 2.03; N, 6.31.

EXAMPLE 14

0 2,2'Bi(2-trifluoromethyl-1,3-dioxolane) (21) and 2- o Trifluoromethyl-2-trifluoroacetyl-1,3-dioxolane (22)

CF$_3$C(O)C(O)CF$_3$+ClCH$_2$CH$_2$OH+NaH→21'22

A mixture of 44.0 g (0.23 mol) of hexafluorobiacetyl, 37.0 (0.46 mol) of 2-chloroethanol, and 150 mL of DMSO was stirred at 15°–20° while 22.1 g (0.46 mol) of 50% NaH in mineral oil were added portionwise. The resulting reaction mixture was then stirred at 20°–25° for one day and then added to 1 L of water. The resulting mixture was extracted with 400, then two 100 mL aliquots, of ether. The ether extracts were washed with 100 mL of water, dried over CaSO$_4$, and the solvent was distilled off. The resulting residue was titrated with 50 mL of petroleum ether, and the resulting solid was recrystallized from a 2:1 mixture of petroleum ether and ether to give 18.8 g of 2,2'-bi(2-trifluoromethyl-1,3-dioxolane), m.p. 88°–90° . A second crop, 7.3 g, m.p. 86°–89° , was obtained by cooling the remaining supernatant which was then filtered to remove this crop. Evaporation of the filtrate and sublimation of the residue at 85° and 0.66 kPa (5 mm) gave another 2.8 g, m.p. 85°–88° , for a total of 28.9 g (45% yield) of the bi(dioxolane) product. An analytical sample, m.p. 88°–90° , was obtained by recrystallization from petroleum ether/ether mixed solvent. IR (CCl$_4$) and NMR (CCl$_4$) spectra for the product were consistent with the assigned structure. Anal.: Calcd. for C$_8$H$_8$F$_6$O$_4$: C, 34.06; H, 2.86; F, 40.40. Found: C, 33.91; H, 2.85; F, 40.16.

Volatiles collected in a −80° trap during the sublimation were 7.9 g (about 13%) of partially hydrated 2-trifluoromethyl-2-trifluoroacetyl-1,3dioxolane. A sample of this material was exposed to moist air until its m.p. rose to a constant value, giving a pure sample of 2-trifluoromethyl-2-trifluoroacetyl-1,3-dioxolane monohydrate, m.p. 102°–103°. IR(CD$_3$CN) and NMR (CD$_3$CN) spectra of the product were consistent with the assigned structure. Anal.: Calcd. for C$_6$H$_6$F$_6$O$_4$: C, 28.14; H, 2.36; F, 4.51. Found: C, 28.04; H, 2.35; F, 44.20.

EXAMPLE 15

2,2-Bis(2-methoxytetrafluoroethyl)-1,3-dioxolane (23)

A mixture of 58 g (about 0.2 mol) of crude bis(2-methoxytetrafluoroethyl) ketone, 16.9 g (0.21 mol) of 2-chloroethanol, and 50 mL of ether was stirred while 29.0 g (0.21 mol) of anhydrous K$_2$CO$_3$ were added in portions with cooling. The resulting reaction mixture was stirred overnight, filtered and distilled to give 40.7 g of 2,2-bis(2-methoxytetra- fluoroethyl)-1,3-dioxolane, b.p. 81° at 40 Pa (0.3 mm), m.p. 39°–40° . Dissolution of the resulting filter cake in water, filtration of the resulting mixture and drying gave another 8.5 g of product, m.p. 38.5°–40° , for a total yield of 49.2 g (74%). IR (CCl$_4$) and NMR (CCl$_4$) of the product were consistent with the assigned structure. Anal.: Calcd. for C$_9$H$_{10}$F$_8$O$_4$: C, 32.35; H, 3.02; F, 45.48. Found: C, 32.14; H, 3.19; F, 45.22.

EXAMPLE 16

2Trifluoromethyl-2-(3-methoxycarbonylperfluoro

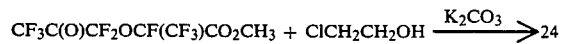

CF$_3$C(O)CF$_2$OCF(CF$_3$)CO$_2$CH$_3$ + ClCH$_2$CH$_2$OH $\xrightarrow{K_2CO_3}$ 24

A mixture of 64.4 g (0.20 mol) of methyl 4-keto-2-trifluoromethylhexafluoro-2-oxahexanoate, 16.1 g (0.20 mol) of 2-chloroethanol, and 100 mL of pentane was stirred with 37.6 g (0.20 mol) of anhydrous K$_2$CO$_3$. Reaction of the starting materials was slow, so 50 mL of ether were added, and the reaction mixture was stirred overnight. The resulting solid mass was titrated thoroughly with 500 mL of ether, filtered and distilled to give 25.9 g 935% yield) of 2-trifluoromethyl-2-(3-methoxycarbonylperfluoro2-oxabutyl)-1,3-dioxolane, b.p. 68°–70° at 0.29 kPa (2.2 mm). IR (CCl$_4$) and NMR (CCl$_4$) spectra of the product were consistent with the assigned structure. Anal.: Calcd. for C$_9$H$_7$F$_9$O$_5$: C, 29.52; H, 1.93; F, 46.70. Found: C, 29.75; H, 2.11; F, 46.41.

EXAMPLE 17

2-Trifluoromethyl-2-pentafluoroethyl-1,3-dioxolane (25)

KF+CF$_2$=CF$_2$+CF$_3$CO$_2$CH$_2$CH$_2$Cl→25

A mixture of 29.1 g (0.50 mol) of dry potassium fluoride' 88.3 g (0.50 mol) of 2-chloroethyl trifluoroacetate, 150 mL of dimethylsulfoxide, and 50 g (0.50 mol) of tetrafluoroethylene was shaken in a 400-mL metal tube at 75° for 18 h. Volatile products were transferred from the reaction mixture held at 43° (1.2 mm). These volatiles were stirred with 500 mL of 10% aqueous NaOH to remove unreacted ester and a small amount of dimethylsulfoxide, then fractionated to afford 61.6 g (47%) of 2-trifluoromethyl-2-pentafluoroethyl-1,3-dioxolane, b.p. 118°–120° . IR (CCl$_4$) and NMR (CCl$_4$) spectra for the product were consistent with the assigned structure. Anal.: Calcd. for $C_6H_4F_8O_2$: C, 27.71; H, 1.55; F, 58.44. Found: C, 27.57; H, 1.65; F, 58.40.

EXAMPLE 18

2-Trifluoromethyl-2-trichloromethoxytetrachloro-1,3 dioxolane (26) and 2-Trifluoromethylpentachloro1,3-dioxolane (27)

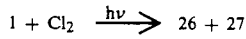

A mixture of 25.8 g (0.15 mol) of 2-methoxy-2-trifluoromethyl-1,3-dioxolane prepared pursuant to a procedure similar to that of Example 1 and 80 mL of $CCl_4$ was stirred in a container equipped with a condenser maintained at $-80°$ while chlorine was bubbled in rapidly enough to maintain the resulting reaction mixture at 65°–70° due to the exothermic reaction. Two h later when the reaction had slowed, sunlamp irradiation was commenced with the continued addition of chlorine. After another 7.75 h, the reaction was completed. Distillation of the reaction mixture gave 12.2 g (26% yield) of 2- c trifluoromethylpentachloro-1,3-dioxolane, b.p. 55°–57° at 1.3 kPa (10 mm). The GC, IR and $^{19}F$ NMR spectra of the product were consistent with the assigned structure. Further fractionation of the remaining reaction mixture gave 33.9 g (55% yield) of 2-trifluoromethyl-2-trichloromethoxytetrachloro-1,3- C dioxolane, b.p. 55°–57° at 27 Pa (0.2 mm). Anal.: Calcd. for $C_5Cl_7F_3O_3$: C, 14.53; Cl, 60.06; F, 13.79. Found: C, 14.46; Cl, 58.94; F, 14.05.

EXAMPLE 19

2-(2-Trichloromethoxycarbonyltetrafluoroethyl)-pentachloro-1,3-dioxolane (28)

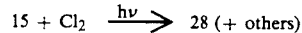

2-Methoxy-Z-(2-methoxycarbonyltetrafluoro-ethyl)-1,3-dioxolane (73.2 g, 0.28 mol) prepared similarly to the procedure in Example 18 was stirred in a container equipped with a condenser maintained at $-80°$ and irradiated with sunlamp while chlorine was passed in at a rate sufficient to cause the temperature of the resulting mixture to rise from 50° to 80° over a 30-h period. Evaporation of volatiles from the resulting crude product gave 144 g of oil, which was indicated by $^{19}F$ NMR to be mainly 2-(2-tri' 10 chloromethoxycarbonyltetrafluoroethyl)pentachloro-1,3-dioxolane.

EXAMPLE 20

2-Methoxycarbonyltetrafluoroethyl)-4,5-dichloro-2,4,5 trifluoro-1,3-dioxolane (29) and 2-(2-Metho carbonyltetrafluoroethyl)-4,4,5-trichloro-2,5-difluoro-1,3-dioxolane (30)

A mixture of 144 g (about 0.28 mol) of crude 2-(2-trichloromethoxycarbonyltetrafluoroethyl)- pentachloro-1,3-dioxolane prepared similarly to the procedure given in Example 19, 100 g (0.56 mol) of flame-dried $SbF_3$, and 2 mL of $SbCl_5$ was stirred and heated. Gas ($COCl_2$) evolution was noticed at 50°–60° during an initial exotherm. The resulting mixture was stirred at 100° for 1 h, after which time 23 mL of liquid had been collected in a $-80°$ trap. The mixture was then refluxed for 1 h while the reactor temperature fell from 119° to 101°. Volatiles (81 g) transferred by warming the reaction mixture at 13 Pa (0.1 mm) were fractionated to give 44.2 g of product, b.p. 103° at 101 kPa (1 atm) to 51° at 1.3 kPa (10 mm). A fraction, b.p. 65°–68° at 13 kPa (100 mm), was shown by IR and $^{19}F$ NMR to be -(2-fluorocarbonyltetrafluoroethyl)-4,5-dichloro2,4,5-trifluoro-1,3-dioxolane (29a). Another fraction , b.p. 56°–56.5° at 2.7 kPa (20 mm), was shown by GC, IR and $^{19}F$ NMR to contain 2-(2-chlorocarbonyltetrafluoroethyl)-4,5-dichloro- 2,4,5-trifluoro-1,3-dioxolane (29b). Still another fraction, b.p. 47°–51° at 10 mm, was shown by GC, IR, and $^{19}F$ NMR to contain 2-(2-chlorocarbonyltetra- fluoroethyl)-4,4,5-trichloro-2,5-difluoro-1,3dioxolane (30a).

The combined acid fluorides and chlorides (44g, about 0.12 mol) whose preparation was described in the preceding paragraph were added dropwise to 19.2 g (24 mL, 0.6 mol) of methanol. The resulting mixture was stirred briefly and distilled to give 20.4 g of 2-(2-methoxycarbonyltetrafluoro-ethyl)-4,5-dichloro-2,4,5-trifluoro-1,3-dioxolane (29) containing some dimethyl tetrafluorosuccinate impurity, b.p. 46°–61° at 0.50 kPa (3.8 mm). The GC IR and NMR spectra of the product were consistent with the assigned structure. Further distillation gave 6.7 g of 2-(2-methoxycarbonyltetrafluoroethyl)4,4,5-trichloro-2,5-difluoro-1,3-dioxolane (30), b.p. 70°–75° at 0.50 kPa (3.8 mm). IR ($CCl_4$) and NMR assigned structure. Anal.: Calcd. for $C_7H_3Cl_3F_6O_4$: C, 22.63; H, 0.81; Cl, 28.63; F, 30.69. Found: C, 22 71; H, 0.79; Cl, 28.31; F, 30.72.

Anal. Calcd. for $C_7H_3Cl_3F_6O_4$: C, 22.63; H, 0.81; Cl, 28.63; F, 30.69. Found: C, 22.71; H, 0.79; Cl, 28.31; F, 30.72.

EXAMPLE 21

2,2-Bis(2-trichloromethoxytetrafluorethyl)-4,4,5,5 tetrachloro 1,3 dioxolane (31)

A solution of 668 g (2.0 mol) of 2,2-bis(2-methoxy-tetrafluoroethyl)-1,3-dioxolane in 1300 mL of $CCl_4$ was stirred and irradiated at 60°–70° for 25 h, then at 70°–80° for 9 h, while chlorine was bubbled in the entire time. Solvent was distilled off, and the resulting residue was heated at 80° at 0.3 mm to give 1330 g (98% yield) of nearly pure 2,2-bis(2-trichloromethoxytetrafluoroethyl) 4,4,5,5-tetrachloro-1,3-dioxolane as a heavy oil. $^1H$ NMR showed no proton present. IR, $^{19}F$ NMR and $^{13}C$ NMR spectra of the product confirmed the structure.

EXAMPLE 22

2-(2-Trichloromethoxytetrafluoroethyl)pentachloro1,3-dioxolane (32)

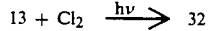

2-Methoxy-2-(2-methoxytetrafluoroethyl) -1,3-dioxolane (47 g, 0.20 mol) was stirred for 45 min while chlorine was bubbled in and a mild exotherm occurred. Addition of chlorine was continued and irradiation with a sunlamp was started. Reaction was continued for 25 h with the temperature slowly raised from 60°–90°. Fractionation of the reaction mixture was accompanied by slow decomposition, so that distillation was stopped after 30.9 g of crude product, b.p. 77.5°–79° at 13 Pa (0.1 mm), were obtained. The resulting distillate was stirred with excess 10% aqueous NaOH and washed with water to give 13.6 g of 2-(2-trichloromethoxytetrafluoroethyl)-pentachloro-1,3-dioxolane as a pale yellow oil. IR (neat): no C=O. NMR (CCl4): $^1$H none; $^{19}$F and $^{13}$C spectra were consistent with the assigned structure. Anal.: Calcd. for $C_6Cl_8F_4O_3$: C, 15.02; Cl, 59.13; F, 15.84. Found: C, 14.74; Cl, 59.12; F, 15.49.

EXAMPLE 23

Fluorination of 2-Trifluoromethyl-2 t:ichloro-etrachloro-1,3-dioxolane

This Example illustrates a use of a product of the invention.

A mixture of 84 g (0.20 mol) of -trifluoromethyl-2-trichloromethoxytetrachloro1,3-dioxolane prepared by a procedure similar to that given in Example 18 and 89.4 g (0.50 mol) of SbF: evolved gas vigorously when 5 mL of SbCl5 was added. After reaction had subsided, the resulting mixture was heated at 75° for 30 min, then at 100° for 1 h, then at reflux for 4 h. Liquid products were transferred under reduced pressure and shown by GC to consist of 96.5% of a mixture of 16.7 g (32% yield) of 2-trifluoromethyl-4,5-dichloro-2,4,5-trifluoro- c 1,3-dioxolane and 33.4 g (59% yield) of -trifluoromethyl-4,4,5-trichloro-2,5-difluoro1,3-dioxolane.

EXAMPLE 24

2-Trifluoromethyl-2-cyanodifluoromethyltetrachloro1,3-dioxolane (33)

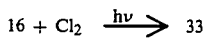

A mixture of 193 g (0.89 mol) and 2-tri-fluoromethyl-2-cyanodifluoromethyl-1,3-dioxolane and 400ml of CCl4 was stirred and irradiated with a sunlamp while chlorine was bubbled in at 60°–70° for 14.5 hr. Distillation of the resulting reaction mixture gave 255.3 g (81%) of 2-trifluoromethyl-2- <>cyanodifluoromethyltetrachloro-1,3-dioxolane, b.p. 58°–59° at 1.3 kPa (10 mm). IR (neat) and NMR - $^{19}$F spectra of the product were consistent with the assigned structure. Anal.: Calcd. for $C_6Cl_4F_5NO_2$: C, 20.31; Cl, 39.96; N, 3.95. Found: C, 20.18; Cl, 40.25; N, 3.74.

EXAMPLE 25

2-Trifluoromethyl-2-cyanodifluoromethyl-4,5-dichloro- o 4,5-difluoro-1,3-dioxolane (34) and 2-Trifluoro-methyl-2 cyanodifluoromethyl-4,4,5-trichloro-5 fluoro 1,3-dioxolane (35)

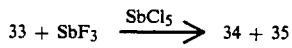

A mixture of 47.2 g (0.13 mol) of 2-tri-fluoromethyl-2-cyanodifluoromethyltetrachloro-1,3dioxolane prepared by a procedure similar to that given in Example 24, 35.8 g (0.20 mol) of SbF3, and 1 mL of SbCl5 was stirred at 100° for 5 hr and at 120° for 6 h. Volatiles were removed under reduced pressure and distilled to give 10.4 g (25%) of 2-trifluoromethyl-2-cyanodifluoromethyl-4,5-dichloro-4,5-difluoro-1,3-dioxolane, b.p. 56°–65° a 13.3 kPa (100 mm). IR (CCl4) and NMR (CCl4) - :"F spectra were consistent with the assigned structure.

Anal.: Calcd. for $C_6Cl_2F_7NO_2$: C, 22.38; Cl, 22.02; N, 4.35. Found: C, 22.50; Cl, 22.31; N, 4.20.

Further distillation gave 24.6 g (56%) of 2-trifluoromethyl-2-cyanodifluoromethyl-4,4,5-trichloro-5-fluoro-1,3-dioxolane, b.p. 53°–54° at 3.3 kPa (25 mm). IR (CCl4) and NMR (CCl4) spectra of this product were consistent with the assigned structure.

Anal.: Calcd for $C_6Cl_3F_6NO_2$: C, 21.29; Cl, 31.43; N, 4.14. Found: C, 21.33; Cl, 31.52; N, 3.67.

EXAMPLE 26

2-Trifluoromethyl-2-cyanodifluoromethyl-4-chloro5-fluoro-1,3-dioxole (36)

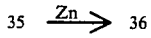

Zinc dust (39.2 g, 0.60 mol) was warmed under vacuum, then blanketed with nitrogen, evacuated, and the process repeated once more. To the zinc dust blanketed with nitrogen were added 250 mL of dry diglyme, 5.0 g (0.02 mol) of iodine, and 3.0 g (0.02 mol) of NaI. The resulting mixture was stirred under $N_2$ until the iodine reacted, and then 73.9 g (0.22 mol) of 2-trifluoromethyl-2-cyanodifluoromethyl-4,4,5-trichloro-5-fluoro-1,3dioxolane were added. The resulting reaction mixture was stirred at 100° for 2 h, after which volatiles were transferred by warming the mixture to 70° at 0.53 kPa (4 mm) pressure. The volatiles were dried over $CaSO_4$, filtered and distilled to give 29.8 g (51% yield) of 2-trifluoromethyl-2-cyanodifluoromethyl-4-chloro-5-fluoro-1,3-dioxole, b.p. 59°–62° (33.2 IR (CCl4) and NMR (CCl4): $^1$H none; $^{19}$F spectra of the product were consistent with the assigned structure. Anal.: Calcd. for C<ClF° NO, C, 26.94; Cl, 13.25; N, 5.24 Found: C, 26.74; Cl, 13.51; N, 4.98.

The early fractions contained appreciable amounts of the 4-hydrodioxole, giving rise to IR spectra containing bands at 3190 (unsat'd) CH and 1775 cm$^{-1}$(C=C) for this monomer.

EXAMPLE 27

Copolymer of 2-Trifluoromethyl-2-cyanodifluoromethyl4-chloro 5-fluoro-1,3-dioxole with Tetrafluoroethylene A 75 mL metal tube charged with 10 g (about of 2-trifluoromethyl-2-cyanodifluoromethyl o-5-fluoro-1,3-dioxole containing 20% of the corresponding 4-hydrodioxole, 17 mL of $CFCl_2CF_2Cl$, 2 mL of 3% perfluoropropionyl peroxide in $CFCl_2CF_2Cl$, and 20 g (0.20 mol) of tetrafluoroethylene was shaken at 40° for 8 h. The resulting mixture was evaporated at 60° and 23 Pa0.2 mm pressure to give copolymer, which was stirred with 100 mL of ether, filtered, rinsed well, and dried under reduced pressure. The resulting solid white copolymer, 2.7 g, softened and melted at 260°–280° on a melting point block. IR(nujol): 2260 cm$^{-1}$ )C=N). Anal.: Calcd for 4-chlorodioxole.16.8 $CF_2=CF_2$: N, 0.72. Found: N, 0.72, 0.71.

IR analysis of the recovered monomers showed no change in ratio of 4-chloro- and 4-hydrodioxoles.

EXAMPLE 28

2-Trifluoromethyl-2-cyanodifluoromethyl-4,5-difluoro1,3-dioxole (37)

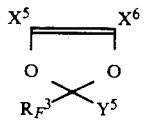

A flask containing 15.0 g (0.63 mol) of magnesium turnings, 0.2 g of mercuric chloride, and 0.2 g of iodine was evacuated to remove air and moisture, then blanketed with nitrogen. Sodium-dried THF, 200 mL, was added, and the resulting mixture was heated to reflux. While the mixture was stirred and refluxed, 32.2 g (0.10 mol) of 2-trifluoromethyl-2-cyanodifluoromethyl-4,5-dichloro-4,5-difluoro-1,3dioxolane were added dropwise over 1.25 h and distillate was taken at 3 times the rate of addition. Methyl iodide (0.1 ml) was injected near the beginning to insure start of reaction. After the addition had been completed, another 25 mL of distillate were taken for a total of 125 mL. The distillate was added to 500 mL of water, and the resulting lower layer was separated, washed with 10 mL of water to give 2.0 g of liquid. GC indicated the presence of 0.7 g (2%) of 2-trifluoromethyl-2- C cyanodifluoromethyl-4,5-difluoro-1,3-dioxole along with starting dioxolane and a trace of 2-trifluoromethyl-2-cyanodifluoromethyl-4-chloro-5-fluoro-1,3-dioxole. The identity of the product was confirmed by IR (CCl$_4$) 1890 cm$^{-1}$(C=C).

What is claimed is:

1. A polymer consisting of dioxole monomer units of the formula

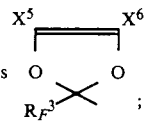

wherein
   $x^5$ and $x^6$ are independently —F or —Cl with at least one being —F;
   $R^3{}_F$ is —F, a perfluorinated alkyl group having 1 to 14 carbon atoms and terminally substituted with —F, —Cl, —OC$_6$F$_5$, —SO$_2$Cl, —SO$_2$F, —CN, —C(O)F or —C(O)OR, or said perfluorinated alkyl group also containing ether oxygen;
   R″ is —CH$_3$, —C$_2$H$_5$ or —CH$_2$CF$_3$;
   Y$^5$ is —F, —R′, Q′, —R or —RC(O)CF$_3$;

Q′ is $$\begin{array}{c} X^5 \underline{\qquad} X^6 \\ O \diagdown \diagup O \\ R_F{}^3 \end{array} ;$$

R′$_F$ is a single bond or a perfluorinated alkyl group having 1 to 4 carbon atoms or said group containing ether oxygen;
with the provisos that
   (a) when R$^3{}_F$ is a perfluorinated alkyl group terminally substituted with —F or —Cl, Y$^5$ is other than —F or —R$^3{}_F$ having terminal substitution with —F or —Cl; and
   (b) when R$^3{}_F$ is —F, Y$^5$ is —R′$_F$Q′.

2. A copolymer of a dioxole of claim 1 and tetrafluoroethylene.

3. A copolymer accordign to claim 2 wherein X$^5$X$^6$ and Y$^5$ are each F.

4. A coating solution comprising a polymer according to claim 2.

5. A coating solution comprising a polymer according to claim 3.

6. A cellulosic substrate coated with a coating solution of claim 4.

7. A cellulosic substrate coated with a coating solution according to claim 5.

8. A film of a polymer of claim 1.

* * * * *